US007725151B2

(12) United States Patent
van der Weide

(10) Patent No.: US 7,725,151 B2
(45) Date of Patent: May 25, 2010

(54) APPARATUS AND METHOD FOR NEAR-FIELD IMAGING OF TISSUE

(76) Inventor: Daniel Warren van der Weide, 4138 Hiawatha Dr., Madison, WI (US) 53711

( * ) Notice: Subject to any disclaimer, the term of this patent is extended or adjusted under 35 U.S.C. 154(b) by 0 days.

(21) Appl. No.: 10/855,686

(22) Filed: May 27, 2004

(65) Prior Publication Data
US 2004/0254457 A1  Dec. 16, 2004

Related U.S. Application Data

(60) Provisional application No. 60/475,181, filed on Jun. 2, 2003.

(51) Int. Cl.
*A61B 5/05* (2006.01)
(52) U.S. Cl. .................. 600/407; 607/101; 607/154
(58) Field of Classification Search ............ 600/443, 600/430, 447, 449, 407, 408, 431, 419, 420, 600/432, 433–435, 421, 425, 427, 411; 606/27–52; 607/101, 154–156; 324/637–648; 424/9.3
See application file for complete search history.

(56) References Cited

U.S. PATENT DOCUMENTS

| | | | | | |
|---|---|---|---|---|---|
| 3,742,235 | A | * | 6/1973 | Boatner et al. | 250/250 |
| 3,812,423 | A | * | 5/1974 | Cronson et al. | 324/638 |
| 3,919,638 | A | * | 11/1975 | Belden, Jr. | 324/95 |
| 4,135,131 | A | * | 1/1979 | Larsen et al. | 324/639 |
| 4,201,986 | A | * | 5/1980 | Ducrocq | 342/100 |
| 4,291,708 | A | * | 9/1981 | Frei et al. | 600/547 |
| 4,458,694 | A | * | 7/1984 | Sollish et al. | 600/547 |
| 4,503,433 | A | * | 3/1985 | Tomasi | 342/87 |
| 4,546,354 | A | * | 10/1985 | Boles | 342/179 |
| 4,546,355 | A | * | 10/1985 | Boles | 342/179 |
| 4,641,659 | A | * | 2/1987 | Sepponen | 600/430 |
| 4,774,961 | A | * | 10/1988 | Carr | 600/549 |
| 5,143,079 | A | * | 9/1992 | Frei et al. | 600/547 |
| 5,363,050 | A | * | 11/1994 | Guo et al. | 324/638 |

(Continued)

OTHER PUBLICATIONS

Charles Capps, "Near field or far field?", Aug. 16, 2001, EDN Magazine.*

(Continued)

*Primary Examiner*—Brian Casler
*Assistant Examiner*—Elmer Chao
(74) *Attorney, Agent, or Firm*—Quarles & Brady LLP

(57) ABSTRACT

Using pulsed or continuous-wave sources, broadband electromagnetic energy generally in the 10 MHz to 300 GHz range is applied through one or a plurality of near-field antennas such as coaxial probe tips. The electromagnetic energy reflected from the surface or transmitted through the near surface of the object (e.g. surface of skin or other tissue or cells) is detected, and the ratio of the test measurement to that from normal tissue is recorded and presented to determine the degree of dielectric contrast, hence inhomogeneity. This degree of contrast is used both on its own and in conjunction with simultaneously acquired optical images to map the boundary of an organ inhomogeneity such as a tumor. The bundle of antennas may be scanned over a surface of the object on a pixel-by-pixel basis to determine the spectra of the sample on a pixel-by-pixel basis, allowing a two dimensional display of the absorption spectra to be provided.

10 Claims, 4 Drawing Sheets

U.S. PATENT DOCUMENTS

| | | | | |
|---|---|---|---|---|
| 5,507,291 | A * | 4/1996 | Stirbl et al. | 600/407 |
| 5,704,355 | A * | 1/1998 | Bridges | 600/407 |
| 5,800,350 | A * | 9/1998 | Coppleson et al. | 600/372 |
| 5,807,257 | A * | 9/1998 | Bridges | 600/430 |
| 5,829,437 | A * | 11/1998 | Bridges | 600/430 |
| 5,854,063 | A * | 12/1998 | Li et al. | 435/287.1 |
| 6,060,915 | A * | 5/2000 | McEwan | 327/94 |
| 6,061,589 | A * | 5/2000 | Bridges et al. | 600/430 |
| 6,064,903 | A * | 5/2000 | Riechers et al. | 600/407 |
| 6,166,542 | A * | 12/2000 | Gallop et al. | 324/300 |
| 6,411,835 | B1 * | 6/2002 | Modell et al. | 600/407 |
| 6,634,244 | B2 | 10/2003 | Radcliffe et al. | |
| 6,671,540 | B1 * | 12/2003 | Hochman | 600/431 |
| 6,678,398 | B2 * | 1/2004 | Wolters et al. | 382/128 |
| 2003/0088180 | A1 * | 5/2003 | Van Veen et al. | 600/430 |

OTHER PUBLICATIONS

Fear et al., Enhancing Breast Tumor Detection with Near-Field Imaging, Mar. 2002, IEEE Microwave Magazine, vol. 2, pp. 48-56.*

E. Pickwell, et al., In vivo study of human skin using pulsed terahertz radiation, Phys. Med. Biol. 49 (2004) pp. 1595-1607, IOP Publishing Ltd., United Kingdom.

* cited by examiner

APPARATUS AND METHOD FOR NEAR-FIELD IMAGING OF TISSUE

CROSS-REFERENCE TO RELATED APPLICATIONS

This application claims the benefit of U.S. provisional application 60/475,181 filed Jun. 2, 2003 entitled Apparatus and Method for Near-Field Imaging of Tissue, hereby incorporated by reference.

FIELD OF THE INVENTION

This invention pertains generally to the field of inspection and identification systems for diseases of epithelial tissue or for pathology of tissue preparations.

BACKGROUND OF THE INVENTION

While visible light and microscopy helps physicians diagnose the presence of many diseases such as carcinomas, pre-carcinomas and other tumors and related skin diseases, as well as pathologies of tissue and cell preparations (e.g. Pap smears), identification of the disease state is still subject to ambiguity. Having both visible (or fluorescent) and alternative imaging means overlaid on the same presentation would enable the physician to more accurately diagnose equivocal presentations. Alternatively, physicians or technicians without the specialized expertise in pathology could be enabled to more accurately diagnose diseases without immediate consultation of a specialist. Furthermore, the sub-surface condition of the tissue, hence the extent and nature of the disease, is very difficult to assess by optical means due to the limited penetration depth and lack of contrast. By using an array of near-field probes or antennas, operating either alone or co-located with an imaging array using visible light, the present invention is a tool for diagnosis of disease and its extent, e.g. tumor boundaries, helping to minimize the pain and disfigurement of surgery used to diagnose and treat tumors and other diseases of the skin, helping to diagnose malformed precancerous cells in Pap smears, and helping to distinguish between normal and cancerous cells in general.

SUMMARY OF THE INVENTION

The present invention provides a new approach to detecting and imaging diseases based on near-field spectroscopic imaging with broadband micro- and and millimeter-wave sources and detectors. "Near field" means imaging at antenna-sample distances generally shorter than the wavelength being used. This enables imaging at spatial resolutions much higher than those normally achievable by conventional far-field imaging. "Spectroscopic imaging" means that absorption, reflection and transmission characteristics of the object are measured and displayed as a function of position. Stimulus and detection technology that has been proven in a wide variety of spectroscopic applications is used in a new application to measure broadband dielectric reflection spectra of tissues or cells using a near-field antenna array.

Short electrical impulses (in the range of 1 to 100 ps) have correspondingly broad frequency spectra, ranging from the microwave through the millimeter-wave regime. Alternatively, frequency-swept or single-frequency sources covering this range or a subset thereof can provide the required stimulus to perform spectroscopic imaging. Electromagnetic energy in this range has shown efficacy in spectroscopic imaging for detecting both surface and sub-surface anomalies, since, for example, tumors and scars of the skin show strong and specific absorption and dispersion in the 0.001-300 GHz range. Gaining spatial resolution at dimensions much smaller than those normally dictated by the wavelengths being used is done with an array of near-field antennas (e.g. coaxial probe tips). Such arrays channel the electromagnetic energy to and from the object (e.g. tissue surface or sub-surface) enabling a new and informative image of the tissue or cells to be formed. With visible (e.g. fiber-optic) imaging co-located with the array, two types of images can be collected simultaneously and overlaid on a computer screen for a more accurate diagnosis. This can be an aid in diagnosing the type and extent of potentially malignant tumors of the skin. Furthermore, the visible imaging ability can enable an accurate mapping of the skin surface so that an irregular scan of the skin will nevertheless build up a fully registered image.

The present invention consists of an array of near-field antennas that can image tissue or cells using the reflection of both visible light and micro- and millimeter-wave signals, which can result from electrical pulses, swept continuous-wave wave (CW) signals, or a combination thereof. Such micro- and millimeter-wave dielectric contrast between cancerous and healthy tissue has been resolved on freshly excised skin tumors using these techniques. While visible light helps physicians diagnose the presence of many tumors, the sub-surface condition of the skin or other tissue, hence the extent of the potential tumor, is difficult to assess, and must usually be diagnosed by surgery, which may require successive biopsies. By using an array of near-field probes, which can be co-located with a means for imaging in the visible or sub-visible illumination, the present invention offers a unique tool for diagnosis of tumor boundaries, reducing the pain and disfigurement of surgery, or speeding the achievement of an accurate diagnosis.

Skin cancer (basal cell carcinoma or BCC) is not only the most common of all cancers, but also is a rapidly growing disease, especially in the United States, where since 1973 the incidence rate for melanoma has more than doubled. While melanoma accounts for only 4% of skin cancers, it causes 79% of deaths from the disease, and 54,200 new cases in the U.S. will be diagnosed in 2003 (American Cancer Society, 2003). Diagnosis of BCC is done visually and with Mohs surgery, which involves repeated removal of tissue and examination under a microscope. Diagnosing the presence of a tumor and knowing its extent without performing surgery would save money, pain and even lives. The need for accurate pathology of specimens in general is extremely high, and even small increments in accuracy will result in lives saved.

Microwave and millimeter waves covering the frequency range from 0.001 to beyond 300 GHz have been used for a variety of medical imaging techniques, but there are few examples of near-field uses, where the lack of deep penetration—normally a hindrance—is a benefit. Skin imaging is one such example. One of the barriers to using this technology for imaging is the cost of the hardware: typical 40 GHz network analyzers from companies like Agilent Technologies cost over $80,000. To build an array of probes for imaging and attach a network analyzer to each probe would be prohibitively expensive. A notable effort to use frequencies much higher than these is the terahertz (THz) imaging technique being promoted by TeraView Ltd in the UK. They have a laboratory system that can distinguish between healthy tissue and basal cell carcinoma, but it costs ~$500 k. There are visible and computer-enhanced visible techniques for imaging and diagnosing diseases of the skin, in particular BCC. These have had limited utility, and have not displaced Mohs surgery as a definitive technique.

Ultrawideband (UWB), carrier-free, impulse, or baseband radar has been rapidly gaining popularity in applications where complex and elusive targets are the norm. UWB radar has benefited from very recent advances in semiconductor technology enabling the production of sub-nanosecond pulses with peak powers of over 1 megawatt but having average powers in the milliwatt regime. The present invention uses picosecond pulses with peak powers less than one watt and average powers in the low milliwatt regime. These power levels are non-ionizing and biologically inconsequential, but because coherent detection can be employed, rejecting noise outside the frequencies of interest, useful spectra can still be measured with them.

The present technology is based on electronic circuits, and has already proven itself in a variety of other spectroscopic applications. Broadband (as opposed to single-wavelength) imaging has the chief advantage of flexibility: differences in skin composition, even on a single patient, can lead to different diagnoses if only a single-wavelength or narrowband source is used. A source with a broad range of frequencies maximizes the opportunity to detect the signature of a surface and even a sub-surface skin anomaly. Furthermore, time-gating of either a real or a synthetic pulse can enable sub-surface spectroscopic imaging while ignoring the return from the surface. With computer-based control, the present technology allows building of a "trainable" detection system with the capability to ultimately learn the signatures of different skin conditions. Furthermore, the advantages of the present approach to screening over other purely-visible imaging techniques include smaller size, lower cost, and potential for integration directly with other imaging modalities such as ultrasound and visible, infrared and ultraviolet imaging techniques such as cameras.

The present invention may be carried out to make broadband dielectric reflection measurements of skin. Spectral measurements can be performed to link the dielectric response to composition of the target. Imaging array techniques can be utilized to improve the detection and location of the target, since fiber-optic light pipes can be used as endoscopes. The integrated-circuit nature of the technology enables arrays to be built as extensions of single-pixel proofs-of-principle.

The present invention is not restricted to imaging of the skin, however. In many surgical procedures on other organs of the body, the extent and nature of a tumor may not be clear even with palpitation and visible observation. In such cases, the present invention may provide a useful adjunct to assist with mapping of the tumor boundaries. The present invention is further useful for examining thin preparations of cells or tissues to determine contrast between normal and transformed (i.e. cancerous) cells, since dielectric contrast exists between the two.

Further objects, features and advantages of the invention will be apparent from the following detailed description when taken in conjunction with the accompanying drawings.

DETAILED DESCRIPTION OF THE INVENTION

Figure 1:
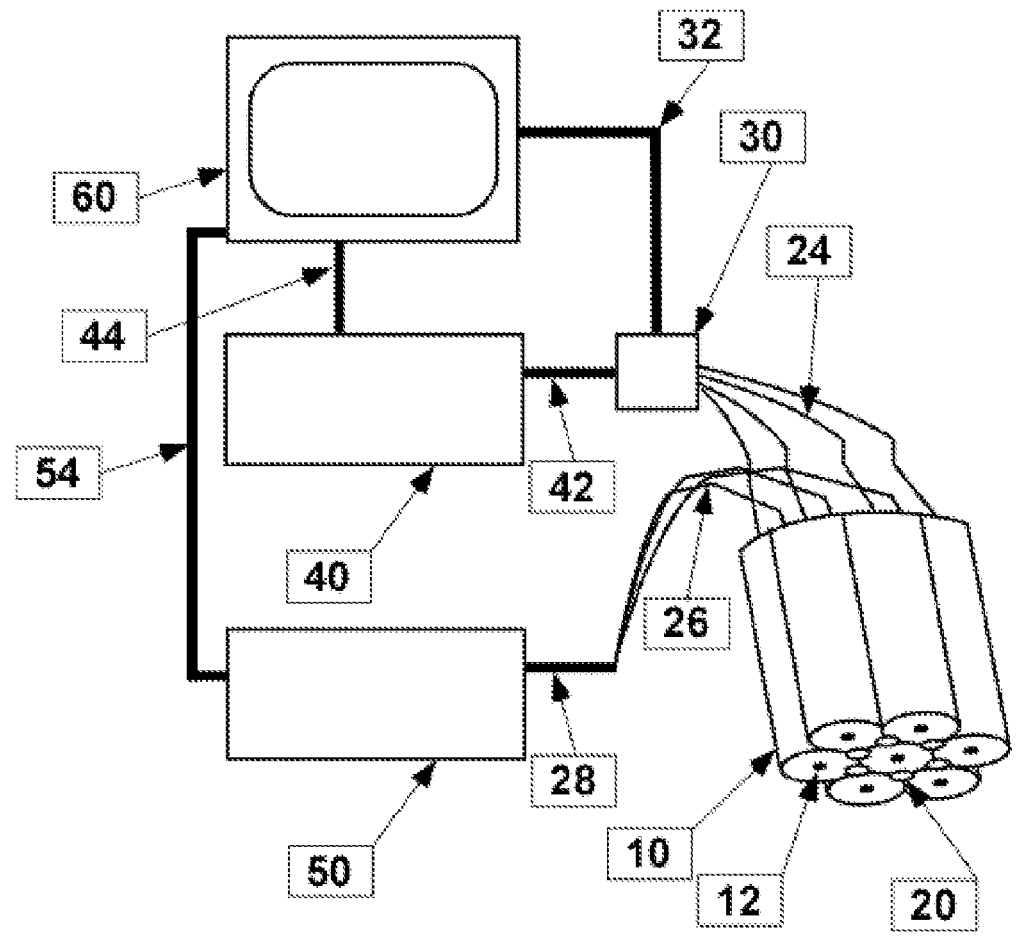
FIG. 1 is a schematic layout of the imaging system illustrating the near-field array and its connection to stimulus and response measurement equipment.

As illustrated in FIG. 1, an array consisting of one or a plurality of near-field antennas or probes such as open-circuited coaxial transmission lines is connected to computer-controlled instrumentation to effect a scanning spectroscopic imaging system. Each coaxial probe consists of an outer conductive shield 10 and inner conductor 12. Fiber-optic light pipes 20 may be interposed and co-located with the coaxial probes to provide simultaneous optical image collection and mapping of the object. The coaxial cables are connected to broadband microwave and millimeter-wave stimulus/response instrumentation 40 via cables 24, and can be multiplexed by a switch array or power combiner/splitter 30. Alternatively, the present invention provides for the use of compact and inexpensive sources and detectors of this broadband energy, eliminating the need for the multiplexer 30. The fiber-optic light pipes 20 are connected to optical instrumentation such as a light source and camera 50 via fibers 26 and connectors 28. Communication with and control of the multiplexing switch or power combiner/splitter 30 by the computer system and display 60 is done through interface 32. Communication with and control of the broadband microwave and millimeter wave instrumentation 40 by the computer system and display 60 is done through interface 44. Communication with and control of the optical imaging instrumentation 50 by the computer system and display 60 is done through interface 54.

Figure 2:
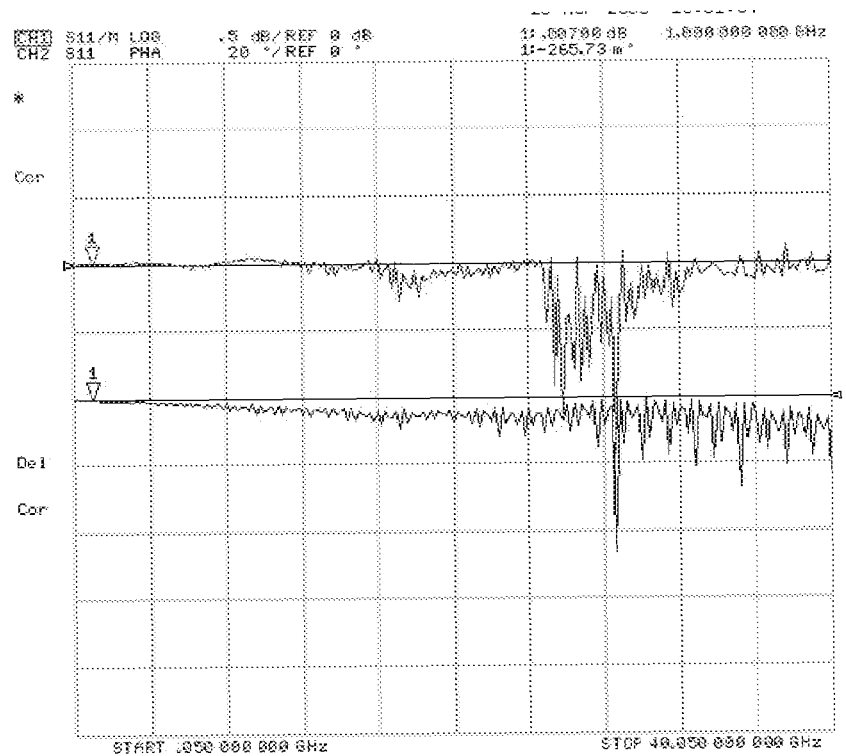
FIG. 2 is a plot of magnitude (above) and phase (below) of the 50 MHz to 40.05 GHz reflection from a squamous cell carcinoma normalized to the reflection from adjacent healthy skin.

As indicated in FIG. 2, a broadband (50 MHz to 40.05 GHz) reflection measurement can be made through a single coaxial probe near-field antenna on a skin tumor, and dielectric contrast between tumor and normal surrounding tissue can be measured. FIG. 2 is the result of a micro- and millimeter-wave reflection measurement made through an open-ended coaxial cable whereby an initial measurement (called the "Reference") is made on healthy skin adjacent to the object (i.e. the tumor). The Reference measurement is stored in memory, the probe moved to a point of interest on the object, and another measurement is made (called the "Test"). The result plotted is the ratio of Test to Reference, both versus frequency. Both Reference and Test consist of one or a plurality of complex wave reflection or transmission coefficients (or their equivalents, e.g. complex impedance) measured at frequencies where dielectric contrast between healthy and abnormal tissue has been found. In the present invention, these frequencies range from 10 MHz to 300 GHz, but are generally between 10 GHz and 40 GHz. Because these measurements are in general complex, the data at each frequency point consists both of a magnitude and of a phase of the wave reflection or transmission. As shown in FIG. 2, both magnitude and phase display deviations from the expected flat line versus frequency, indicating that the Test measurement and the Reference measurement were made on an inhomogeneous sample having different properties (dielectric contrast) versus position of the coaxial probe. This observation is the core of the present invention, namely that such dielectric contrast when presented as a spectroscopic image, can aid in the diagnosis and mapping of skin tumors.

Figure 3:
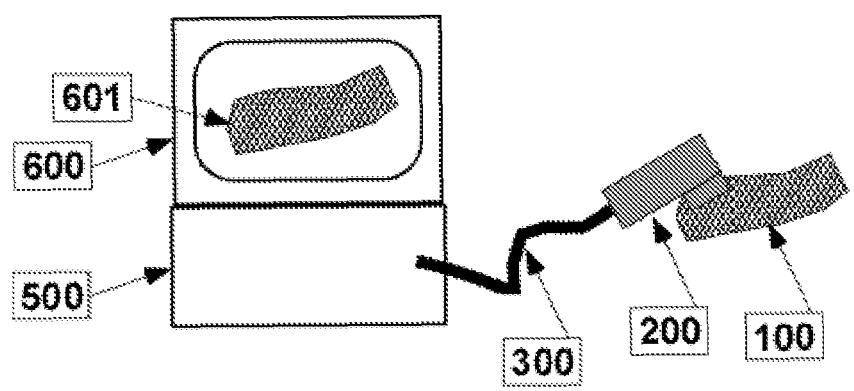
FIG. 3 is a schematic diagram of apparatus for conducting reflection measurements on an object in accordance with the invention.
Figure 4:
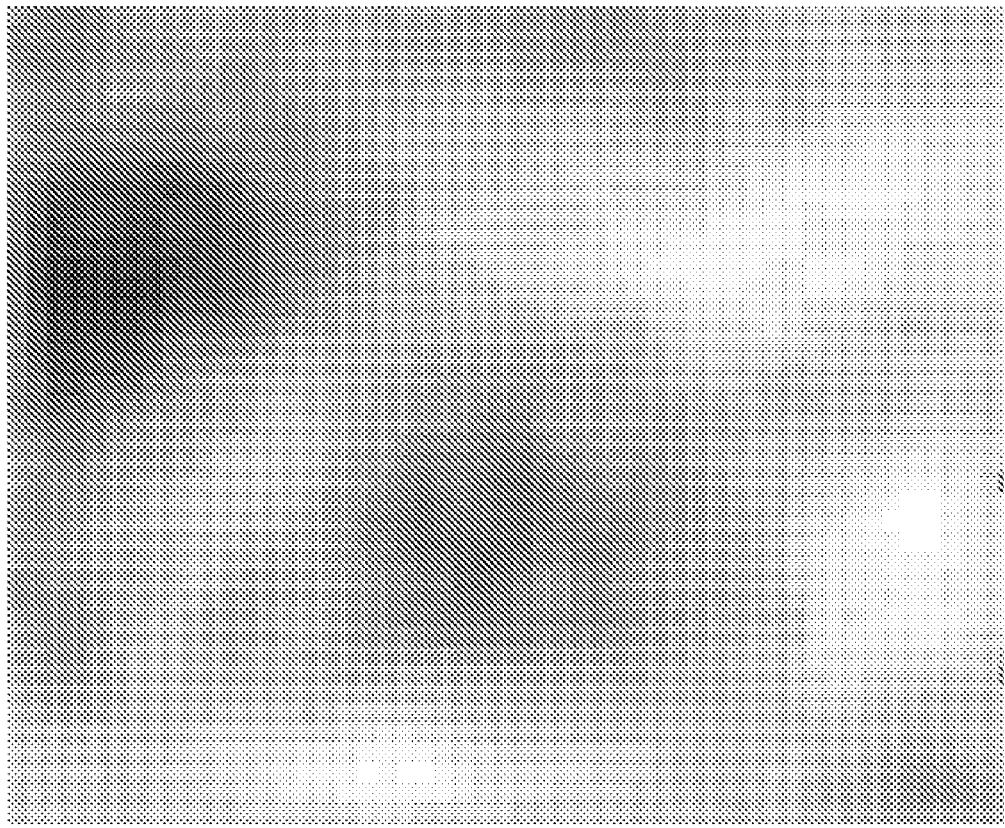
FIG. 4 is a photographic close-up of a large cell neoplasm, a remnant of cancerous skin tissue.
Figure 5:
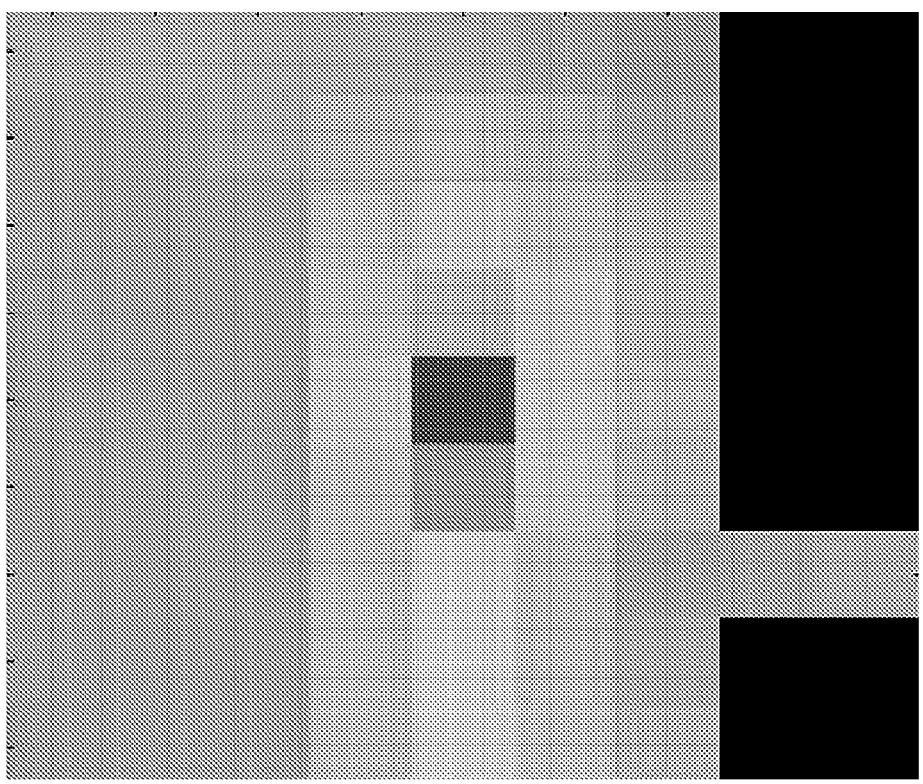
FIG. 5 is the same area of the skin as FIG. 4, but scanned with the apparatus of the present invention. The contrast of the cancerous lesion against the background of normal skin is evident, and is in registration with the photographic image of FIG. 4. Note that the right-most coaxial microwave probe is disabled for a portion of the scan, further indicating contrast between an activated probe in contact or near-contact with the tissue and a disabled probe.

FIG. 3 shows how the present invention can be used in a preferred embodiment. The object (e.g. skin or other organ with inhomogeneities) 100 is scanned with a head 200 containing one or a plurality of broadband near-field antennas, possibly also containing fiber light pipes for simultaneous collection of a visible image; this collection will be hereinafter referred to as the "antenna bundle". First, and periodically, the near-field image of normal skin (preferably adjacent to the object under examination) is taken and stored. Then the head 200 is scanned over the object, the measurement is made and a normalized measurement plotted on the display 600. The head 200 provides a means for convenient positioning and hand-scanning of the antenna bundle, but the head could also be mounted onto a remote-actuated lever or stage for use inside a body cavity or for use in telemedicine. The head 200 is connected to an instrument cluster 500 through a bundle of cables and (if needed) fibers 300. Depending on the specific implementation, the broadband sources and/or detectors and, if needed, the optical imaging sources and detectors (hereinafter called the "instrument bundle") could be co-located with the antenna bundle in the head 200, or they could be addressed through a switch (multiplexer), in which case the instrument bundle would be in the instrument cluster 500. Control of the instrument bundle, acquisition of both broadband and optical images, and display of same is accomplished through computer system 600. Combinations of broadband and optical images can be stored, retrieved, and overlaid with each other for aid in diagnosis and mapping of tumor boundaries.

As shown in FIG. 3, the head 200 containing the antenna bundle presents a flat surface to the object being scanned (e.g. skin or a microscope slide with a thin preparation of cells or tissue). Variations in contact pressure of the head 200 on the skin could cause variations in the broadband coupling of the antennas to the tissue, altering the image in an inconsistent fashion. A pressure sensor embedded in the head can be used to monitor the pressure of the head 200 on the tissue, and a simple light- or tone-based feedback mechanism could be employed to help the operator maintain constant pressure. Alternatively, an automatic control system could maintain constant pressure by moving the antenna bundle into and out of the center of a larger ring that would make more stable contact with the skin.

Normalized measurements of reflection spectra to and from one particular near-field antenna give results like those in FIG. 2 when a tumor or other densely-packed tissue is being examined. These can be extended to transmission spectra if the stimulus emanates from one antenna and is picked up by one or more nearby antennas. This technique not only promotes imaging more deeply into the tissue (since the waves must travel farther), but also conveniently eliminates the need for a wave-separation device (e.g. a directional coupler) in the instrument bundle. It is an object of the present invention that both modes of operation are possible and of specific utility.

The measurement shown in FIG. 2 is a single-pixel result of what would be presented as an image on the system display. An algorithm examines the deviation from normal reflection (in magnitude and/or phase) versus frequency at one or a plurality of frequencies, and in a preferred embodiment, assigns a color to this level of deviation, such that the degree of deviation is presented to the operator as a "false-color" map of the area that is scanned. Single points can also be measured with the array (whose element numbers can range from 1 to >100), such that spot measurements can be taken with no need for presenting an image. In this case, a simple "red-yellow-green" light display can be employed.

Further examples illustrating the invention are set forth below.

To examine the contrast between normal skin and scar tissue, the procedure of taking and storing a normal skin measurement (Reference) was performed. Then the coaxial probe was placed onto adjacent, healed, scar tissue whose surface was slightly raised, but whose color was nearly identical to that of adjacent skin. Significant and repeatable contrast in the ratio Test/Reference was observed, while for Test measurements made on other normal skin, the contrast was nearly unmeasurable.

To examine the contrast between normal skin and common small moles (diameter ~1 mm), the procedure of taking and storing a normal skin measurement (Reference) was performed. Then the coaxial probe was placed onto a mole whose color was distinct from that of adjacent skin. Otherwise, the mole was impalpable. Insignificant contrast in the ratio Test/Reference was observed, indicating that a simple change in pigmentation is ignored by the present invention, unless it is detected by the optical sensing capabilities of the fiber optics.

The images collected with the present invention can be stored in a computerized database. They can be abstracted and compared with other images, either of similar diagnoses or of contrasting diagnoses. This database can contain not only comments from pathologists but also the abstracted images accessed by an "expert system" algorithm to assist in diagnosis. The database can be accessed via local networks or via the Internet, with proper security implemented. Such a database when connected to the instrument in a "live" measurement can help immediate diagnosis, effectively providing a "second opinion."

It is understood that the invention is not limited to the embodiments set forth herein as illustrative, but embraces all such forms thereof as come within the scope of the following claims.

What is claimed is:

1. A method for detection of dielectric anomalies at the surface of human or animal organs, including the skin, other tissues and cells, comprising:
   (a) applying electromagnetic energy through an array comprising a plurality of closely-spaced coaxial near-field probes each having a center conductor and a coaxial shield, each center conductor terminated in a tip that is substantially flat and flush with adjacent tips to provide a flat surface positionable substantially in contact with the surface using electrical pulses or continuous-wave excitation with one or a multiplicity of frequencies having content in the range of 10 MHz to 300 GHz at an object positioned on the surface of a human or animal organ;
   (b) acquiring the reflection or transmission coefficient spectra or both from the object; and
   (c) reconstructing from the acquired reflection or transmission coefficient spectra an image of the object at antenna sample distances shorter than the wavelength of the electromagnetic energy.

2. The method of claim 1 wherein steps (a) and (b) are repeated on a pixel-by-pixel basis over the surface of an object.

3. The method of claim 1, further comprising the step of assigning to the spectra or a portion thereof different colors to represent different values of the spectra, resulting in an image-like presentation that indicates dielectric contrast.

4. The method of claim 3 wherein the electromagnetic radiation is applied in pulses with a frequency synthesizer.

5. The method of claim 3 wherein applying electromagnetic radiation in pulses is carried out utilizing a pulse generator.

6. The method of claim 3 wherein acquiring the reflection or transmission spectra or both from the sample is carried out utilizing a diode detector.

7. The method of claim 3 wherein acquiring the reflection or transmission spectra or both from the sample is carried out utilizing a bolometric detector.

8. The method of claim 3 wherein acquiring the reflection or transmission spectra or both from the sample is carried out utilizing a diode sampler as the detector.

9. The method of claim 3 wherein acquiring the reflection or transmission spectra or both from the sample is carried out utilizing a frequency mixer as the detector.

10. The method of claim 3, wherein the image-like presentation is produced contemporaneously with the reflection or transmission coefficient spectra.

* * * * *